(12) United States Patent
Alizoti et al.

(10) Patent No.: US 9,642,980 B2
(45) Date of Patent: May 9, 2017

(54) VENTILATOR CIRCUIT, ADAPTER FOR USE IN VENTILATOR CIRCUIT AND METHODS FOR THE USE THEREOF

(71) Applicant: TRUDELL MEDICAL INTERNATIONAL, London (CA)

(72) Inventors: Neritan Alizoti, London (CA); James Schmidt, London (CA)

(73) Assignee: Trudell Medical International, London (CA)

( * ) Notice: Subject to any disclaimer, the term of this patent is extended or adjusted under 35 U.S.C. 154(b) by 467 days.

(21) Appl. No.: 14/212,628

(22) Filed: Mar. 14, 2014

(65) Prior Publication Data

US 2014/0360498 A1    Dec. 11, 2014

Related U.S. Application Data

(60) Provisional application No. 61/791,904, filed on Mar. 15, 2013.

(51) Int. Cl.
*A61M 16/14* (2006.01)
*A61M 16/08* (2006.01)
(Continued)

(52) U.S. Cl.
CPC .......... *A61M 16/14* (2013.01); *A61M 11/00* (2013.01); *A61M 15/00* (2013.01); *A61M 15/009* (2013.01); *A61M 15/0025* (2014.02); *A61M 15/0065* (2013.01); *A61M 16/0816* (2013.01); *A61M 16/0833* (2014.02); *A61M 16/20* (2013.01); *A61M 16/208* (2013.01); *A61M 11/005* (2013.01); *A61M 11/007* (2014.02); *A61M 11/06* (2013.01); (Continued)

(58) Field of Classification Search
CPC .............. A61M 16/08; A61M 16/0816; A61M 16/0833; A61M 16/0866; A61M 16/0875; A61M 16/14; A61M 16/208
See application file for complete search history.

(56) References Cited

U.S. PATENT DOCUMENTS

| 584,091 A | 6/1897 | Leidich |
| 2,688,979 A | 9/1954 | Kendrick |

(Continued)

FOREIGN PATENT DOCUMENTS

| EP | 1066850 B1 | 8/2006 |
| GB | 558607 | 1/1944 |

(Continued)

*Primary Examiner* — Valerie L Woodward
(74) *Attorney, Agent, or Firm* — Brinks Gilson & Lione

(57) ABSTRACT

An adapter includes a housing having an inlet port defining a flow path and an outlet port. An interior wall has an inner surface defining an interior passageway communicating with the outlet port and an exterior surface defining an exterior passageway communicating with the inlet port. The interior wall defines a mouth communicating between the interior and the exterior passageways. The interior wall is positioned transverse to the flow path of the inlet port. A medicament delivery port opens into the mouth. A valve is moveable between a closed position, wherein the valve closes the medicament delivery port, and an open position, wherein the medicament delivery port is open. A ventilator circuit and method of delivering a medicament are also provided.

23 Claims, 22 Drawing Sheets

(51) Int. Cl.
  *A61M 16/20* (2006.01)
  *A61M 11/00* (2006.01)
  *A61M 15/00* (2006.01)
  A61M 11/06 (2006.01)
  A61M 16/04 (2006.01)

(52) U.S. Cl.
  CPC ..... *A61M 15/0085* (2013.01); *A61M 16/0463* (2013.01); *A61M 2202/0208* (2013.01); *A61M 2205/02* (2013.01)

(56) References Cited

U.S. PATENT DOCUMENTS

| | | | |
|---|---|---|---|
| 2,710,623 A | 6/1955 | Kolos | |
| 2,822,819 A | 2/1958 | Geeraert | |
| 3,174,434 A | 3/1965 | Schieve | |
| 4,930,498 A | 6/1990 | Hayek | |
| 4,938,210 A | 7/1990 | Shene | |
| 4,951,661 A * | 8/1990 | Sladek | A61M 16/0808 128/202.27 |
| 5,164,740 A | 11/1992 | Ivri | |
| 5,241,954 A | 9/1993 | Glenn et al. | |
| 5,396,883 A | 3/1995 | Knupp et al. | |
| 5,443,452 A | 8/1995 | Hart et al. | |
| 5,461,695 A | 10/1995 | Knoch | |
| 5,586,550 A | 12/1996 | Ivri et al. | |
| 5,696,883 A | 12/1997 | Arima | |
| 5,758,637 A | 6/1998 | Ivri et al. | |
| 5,938,117 A | 8/1999 | Ivri | |
| 6,014,970 A | 1/2000 | Ivri et al. | |
| 6,014,972 A | 1/2000 | Sladek | |
| 6,085,740 A | 7/2000 | Ivri et al. | |
| 6,205,999 B1 | 3/2001 | Ivri et al. | |
| 6,367,470 B1 | 4/2002 | Denyer et al. | |
| 6,382,255 B2 | 5/2002 | McFarland | |
| 6,412,481 B1 * | 7/2002 | Bienvenu | A61M 15/0086 128/200.21 |
| 6,615,824 B2 | 9/2003 | Power | |
| 6,629,646 B1 | 10/2003 | Ivri | |
| 6,701,922 B2 | 3/2004 | Hindle et al. | |
| 6,725,858 B2 | 4/2004 | Loescher | |
| 6,948,591 B2 | 9/2005 | Scott et al. | |
| 6,968,840 B2 | 11/2005 | Smith et al. | |
| 7,100,600 B2 | 9/2006 | Loeffler et al. | |
| 7,201,167 B2 | 4/2007 | Fink et al. | |
| 7,267,121 B2 | 9/2007 | Ivri | |
| 7,290,541 B2 | 11/2007 | Ivri et al. | |
| 7,322,349 B2 | 1/2008 | Power | |
| 7,600,511 B2 | 10/2009 | Power et al. | |
| 7,669,595 B1 * | 3/2010 | Mitchell | A61M 11/06 128/200.14 |
| 7,686,014 B2 | 3/2010 | Boehm et al. | |
| 7,971,588 B2 | 7/2011 | Fink et al. | |
| 8,746,241 B2 * | 6/2014 | Cavendish | A61M 16/0816 128/202.27 |
| 2002/0134374 A1 | 9/2002 | Loeffler et al. | |
| 2002/0134375 A1 | 9/2002 | Loeffler et al. | |
| 2002/0162554 A1 * | 11/2002 | Loescher | A61M 16/08 128/205.24 |
| 2003/0222238 A1 | 12/2003 | Getzewich et al. | |
| 2004/0096402 A1 | 5/2004 | Hodges et al. | |
| 2005/0217666 A1 | 10/2005 | Fink et al. | |
| 2005/0229927 A1 | 10/2005 | Fink et al. | |
| 2007/0240709 A1 * | 10/2007 | Woolley | A61M 16/08 128/200.21 |
| 2008/0027372 A1 | 1/2008 | Baldwin | |
| 2008/0210242 A1 * | 9/2008 | Burk | A61M 16/06 128/206.21 |
| 2009/0025722 A1 | 1/2009 | Pieper et al. | |
| 2010/0126502 A1 | 5/2010 | Fink et al. | |
| 2011/0011395 A1 * | 1/2011 | Mazela | A61M 16/0816 128/202.13 |
| 2013/0126011 A1 * | 5/2013 | Abraham | F16K 13/00 137/315.01 |

FOREIGN PATENT DOCUMENTS

| | | |
|---|---|---|
| WO | WO 97/29799 A2 | 8/1997 |
| WO | WO 01/83011 A1 | 11/2001 |
| WO | WO 03/059413 A2 | 7/2003 |
| WO | WO 2007141201 A1 | 12/2007 |

* cited by examiner

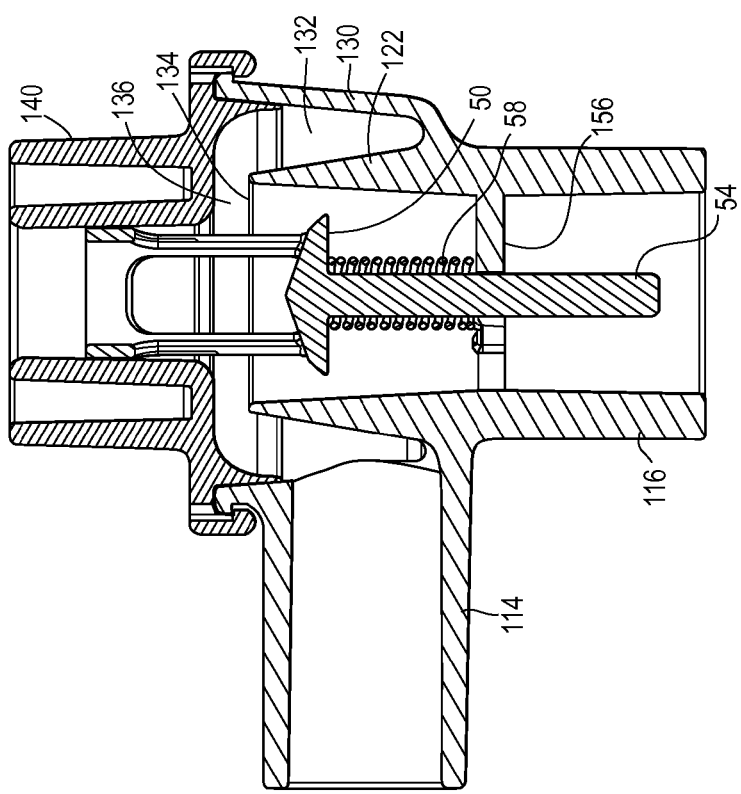
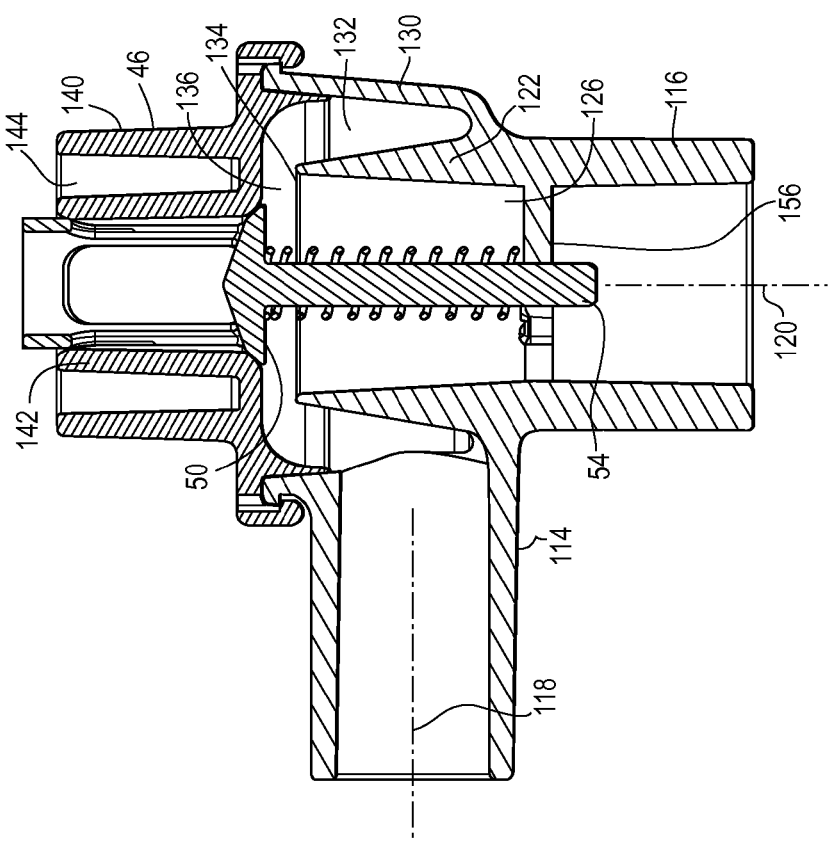

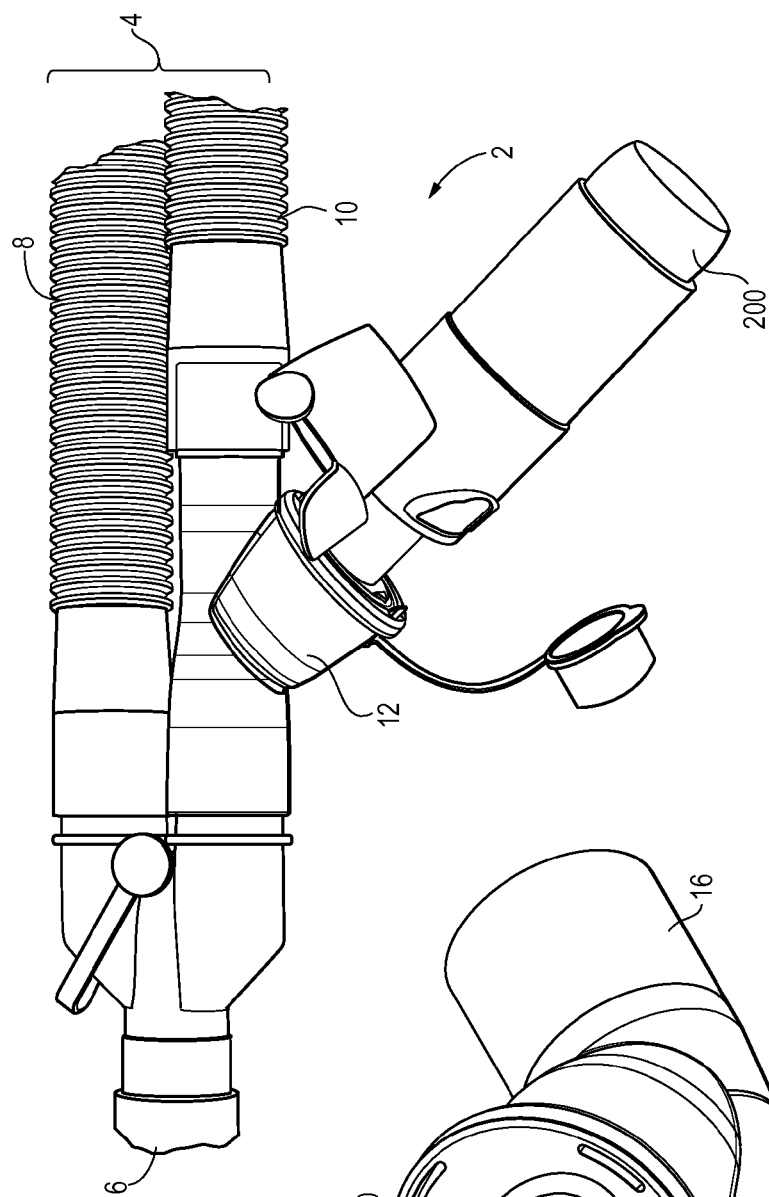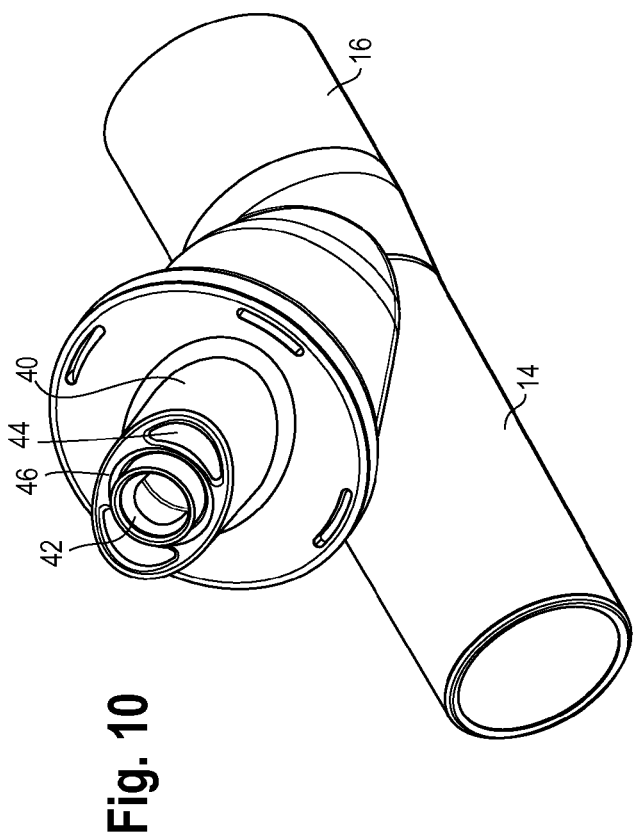

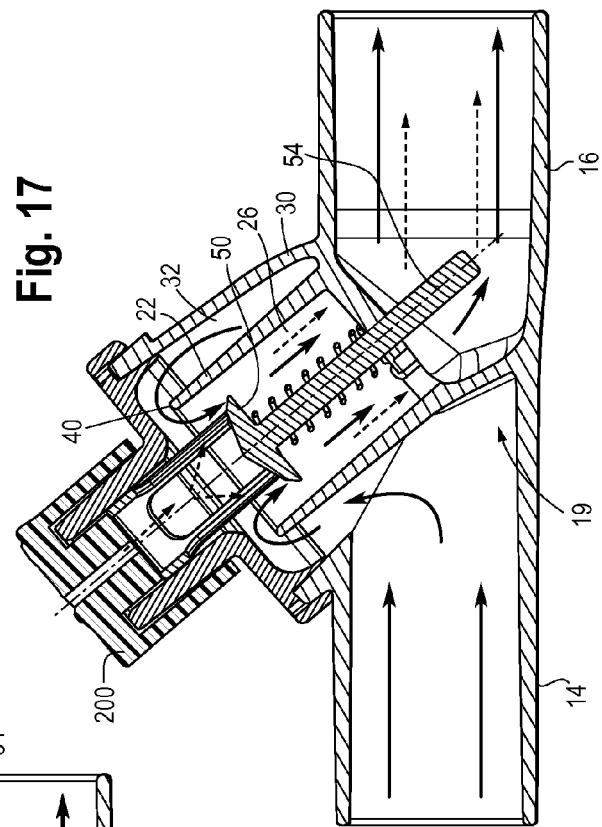
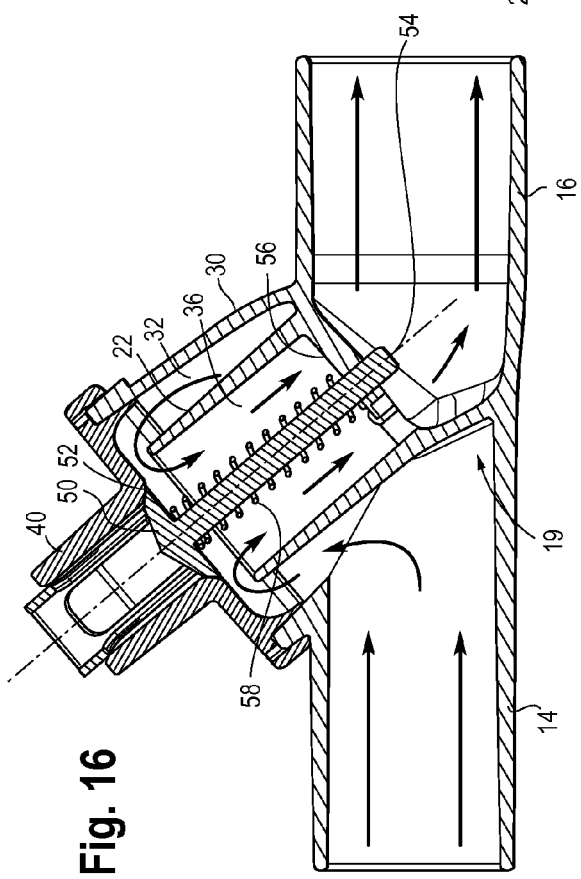

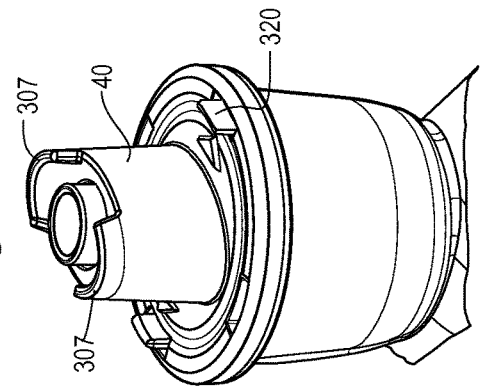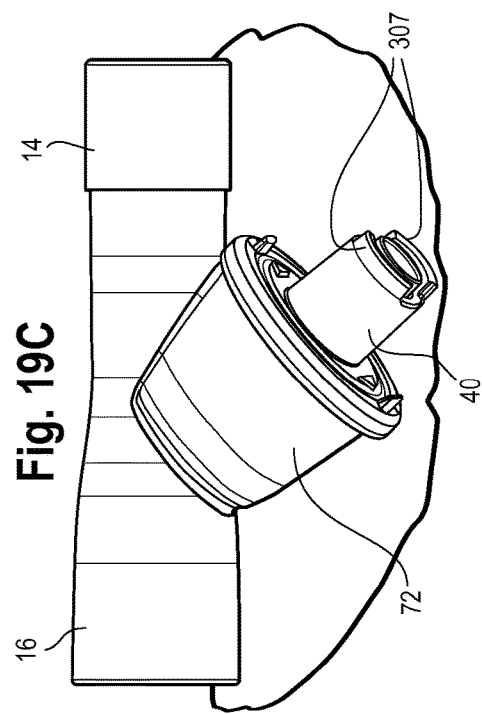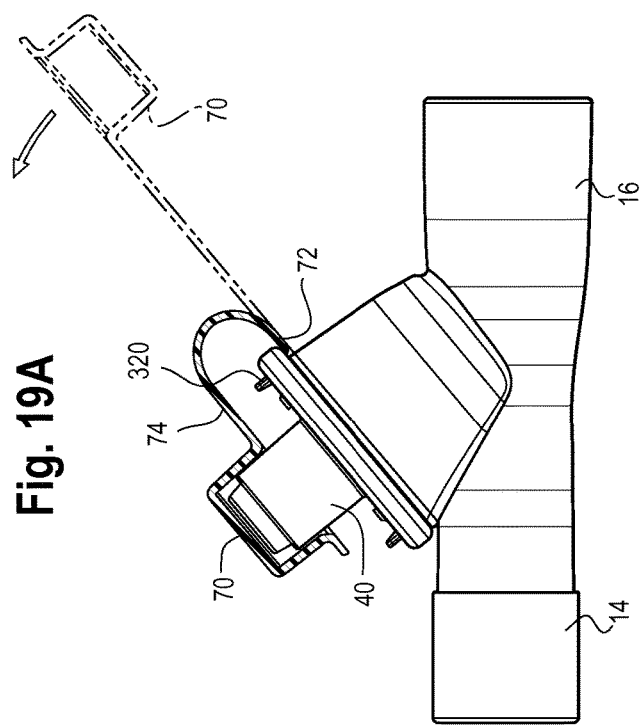

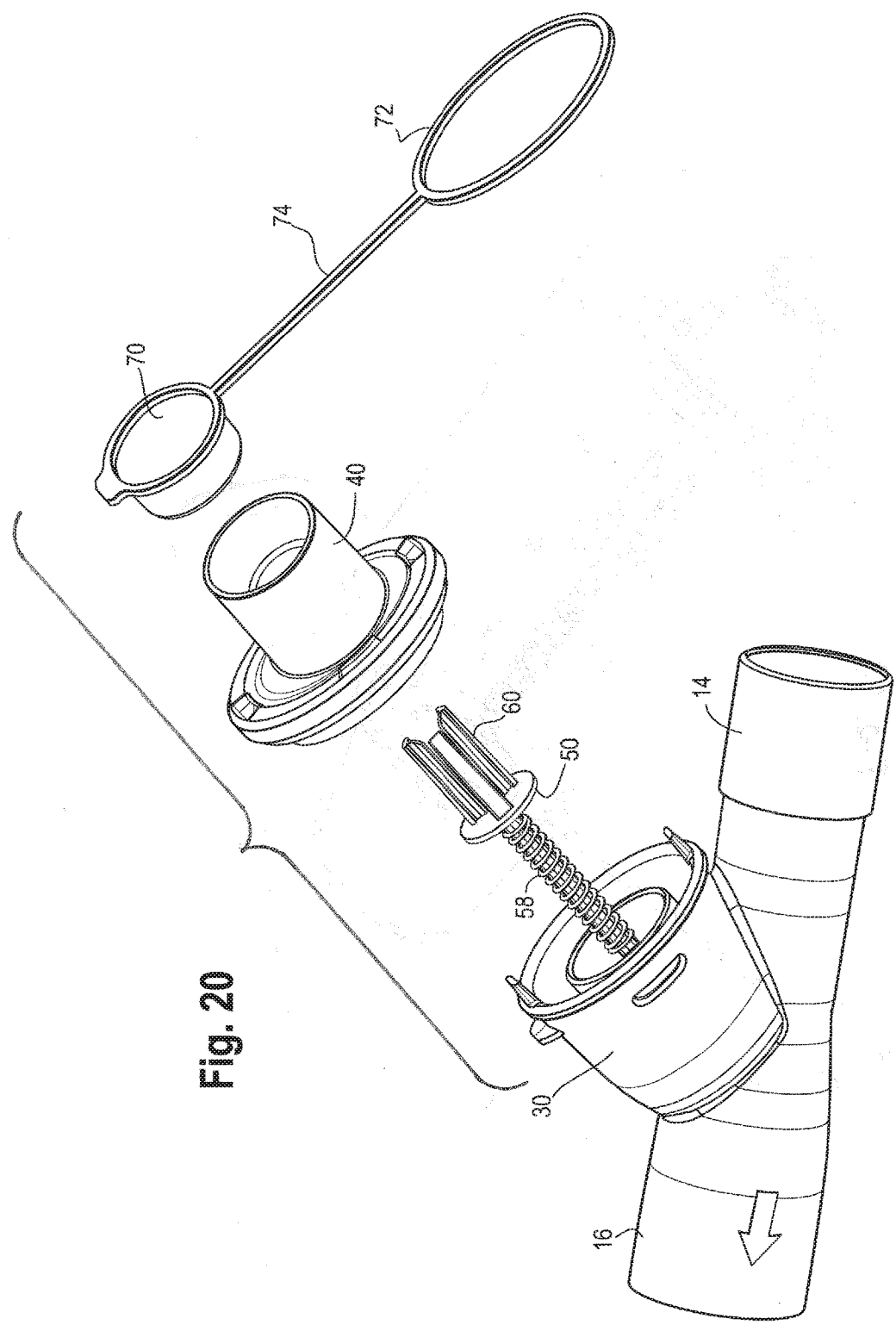

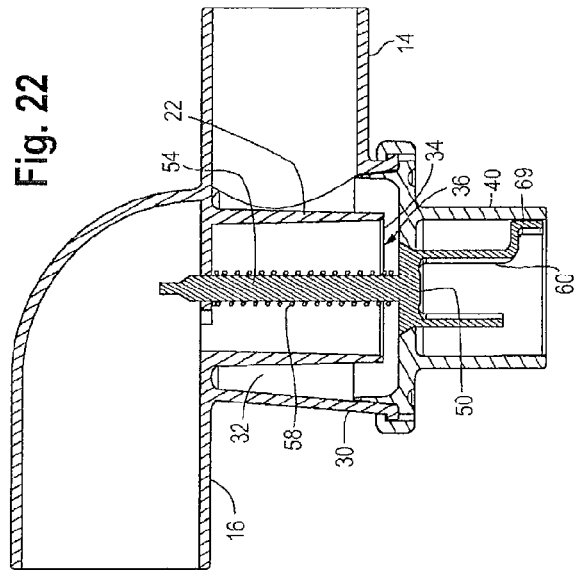
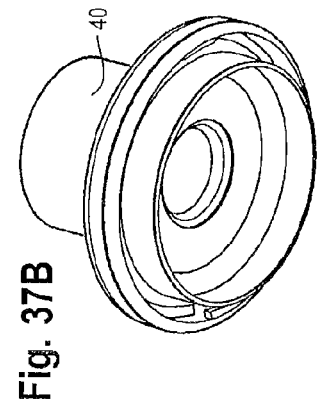
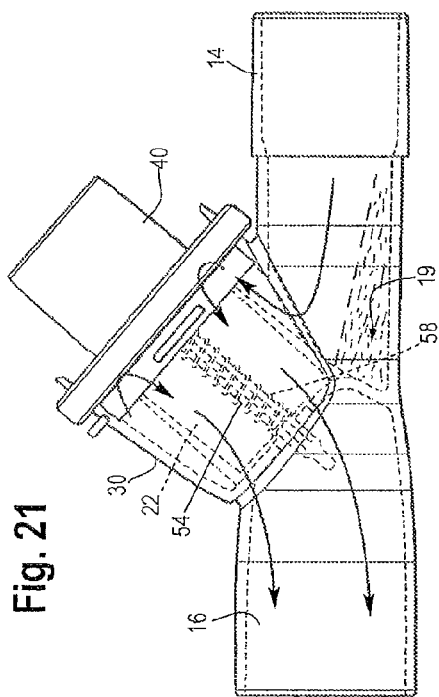
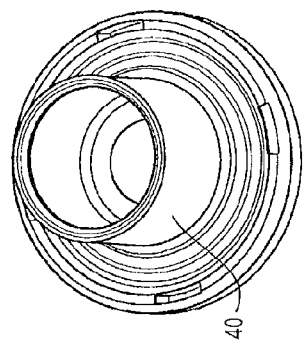
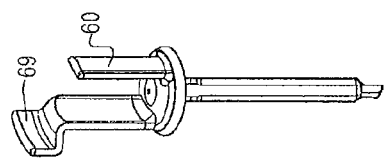

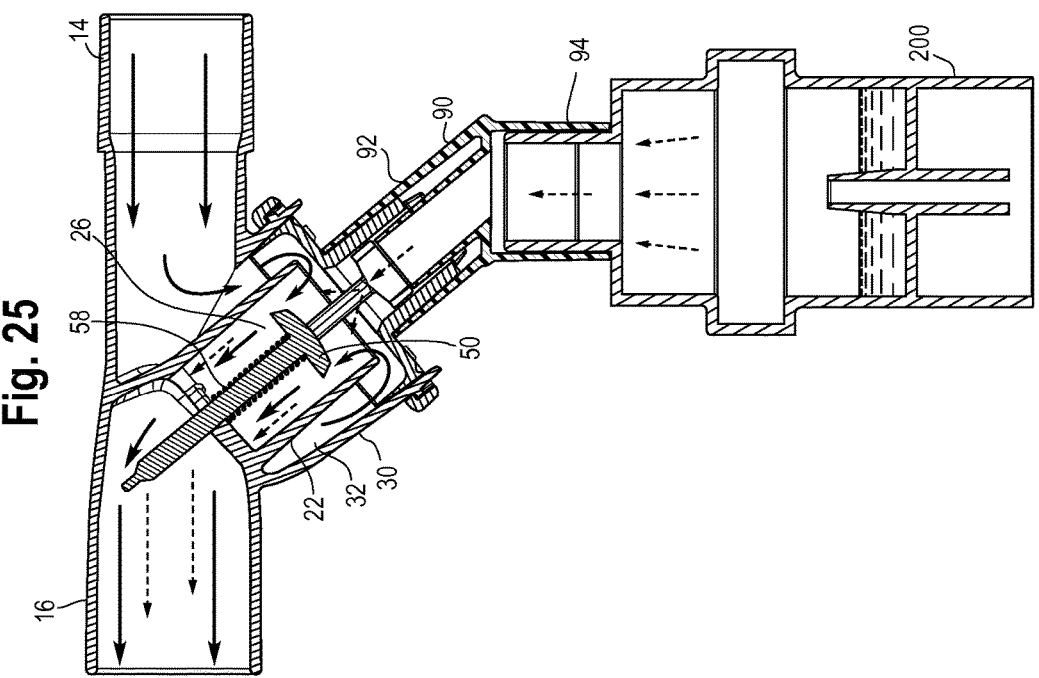
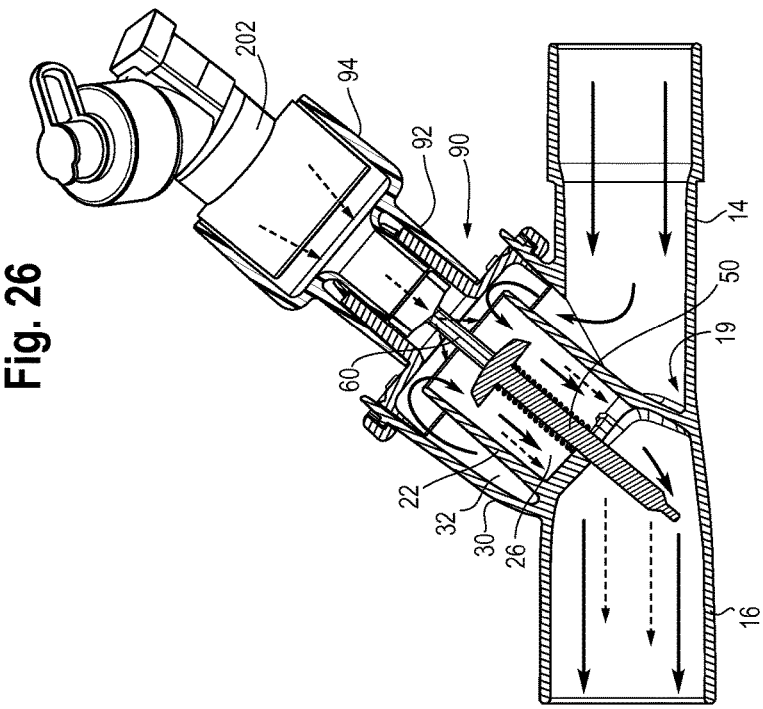
Fig. 25
Fig. 26

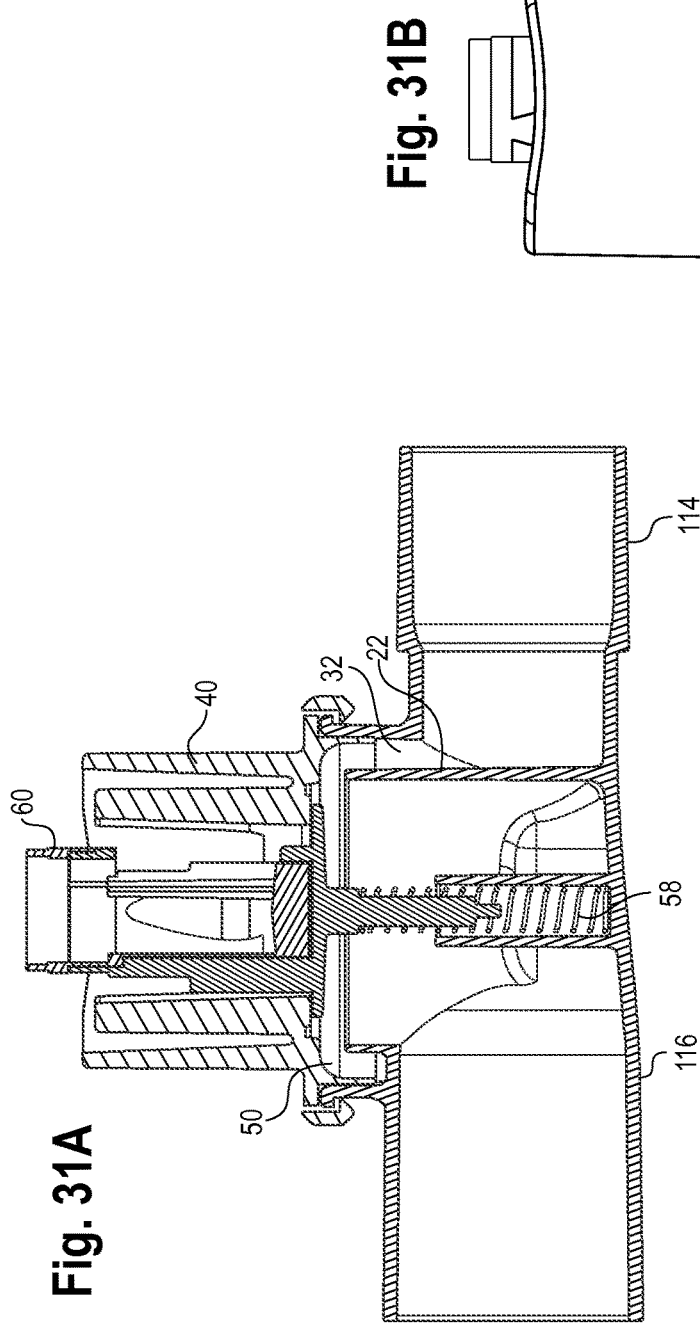
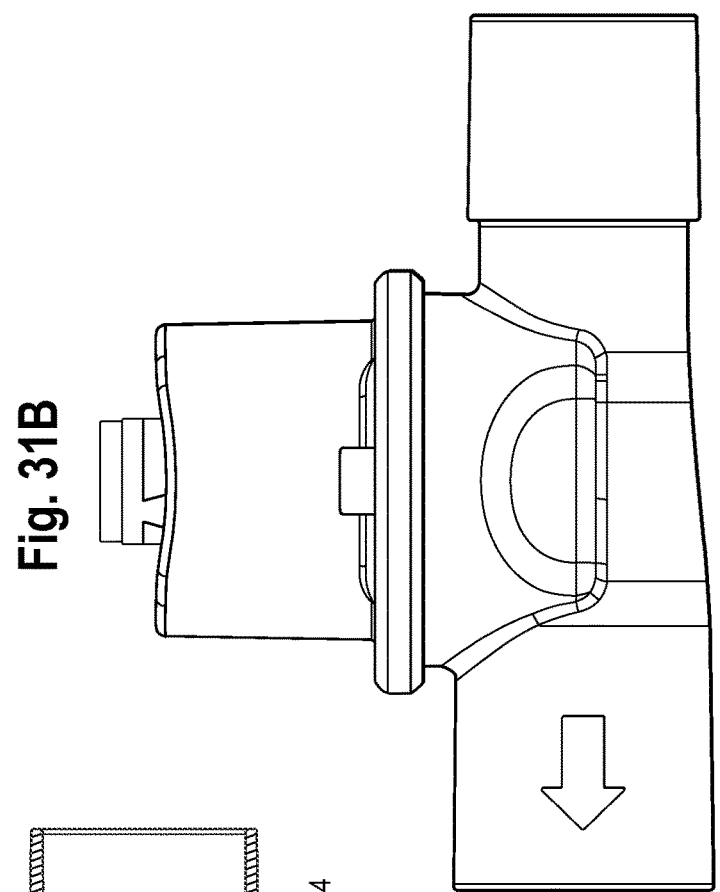

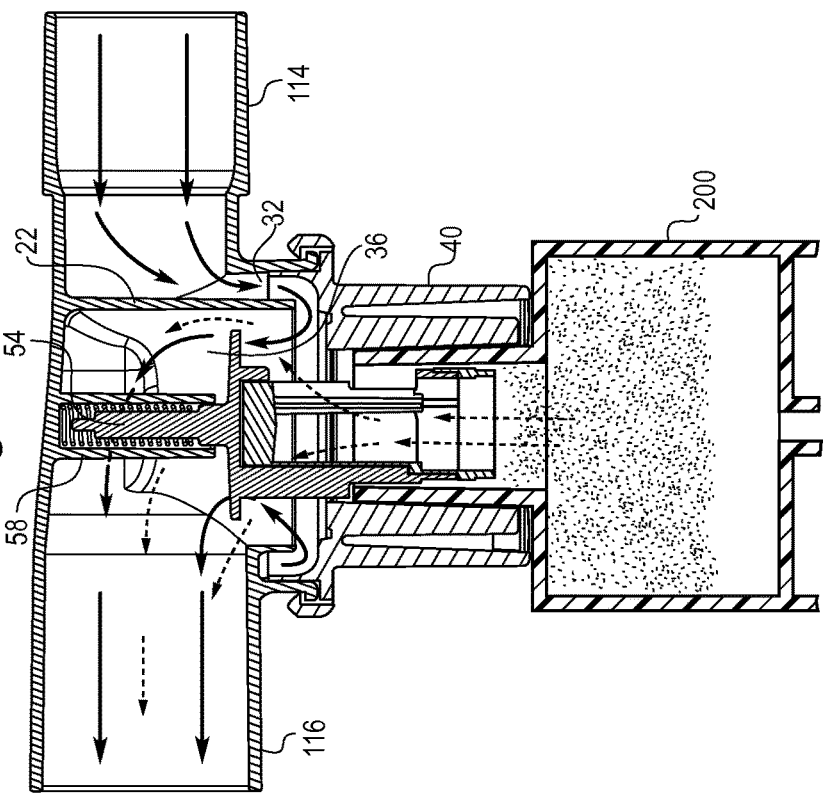
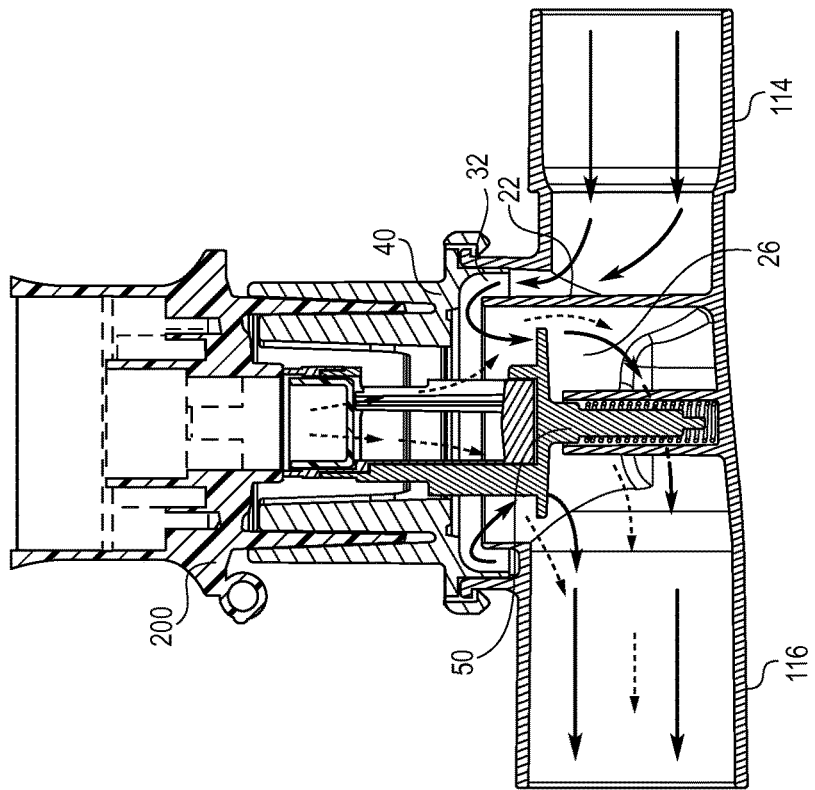

VENTILATOR CIRCUIT, ADAPTER FOR USE IN VENTILATOR CIRCUIT AND METHODS FOR THE USE THEREOF

This application claims the benefit of U.S. Provisional Application No. 61/791,904, filed Mar. 15, 2013, the entire disclosure of which his hereby incorporated herein by reference.

TECHNICAL FIELD

The present invention relates generally to an adapter for delivering a medicament in ventilator circuit, and to a ventilator circuit and methods for the use thereof.

BACKGROUND

It is well known to deliver aerosolized medicaments to a patient via various devices, including nebulizers and aerosol dispensing devices, such as pressurized Metered Dose Inhalers (PMDI's), in order to treat various conditions and diseases, including but not limited to various respiratory conditions and diseases such as asthma. Often, it is desirable and necessary to deliver such medicaments to a patient interfacing with a ventilator circuit. To provide such medicaments, an adapter may be positioned within the circuit to provide access for a medicament delivery device. Known adapters, however, are not suitable for interfacing with various medicament delivery devices Respimat Soft Mist Inhaler. In addition, such adapters typically are not self-sealable, but instead require a sealing cap to be re-placed after each use in order to seal the ventilator circuit from leaks or contamination In addition, while some known adapters may allow for the introduction of a medicament into a ventilator gas flow, the medicament may not be fully entrained or mixed, thereby reducing the amount of uniformity in the drug delivery to the patient.

SUMMARY

Briefly stated, in one aspect, one embodiment of an adapter includes a housing having an inlet port defining a flow path and an outlet port. An interior wall has an inner surface defining an interior passageway communicating with the outlet port and an exterior surface defining an exterior passageway communicating with the inlet port. The interior wall defines a mouth communicating between the interior and the exterior passageways. The interior wall is positioned transverse to the flow path of the inlet port. A medicament delivery port opens into the mouth. A valve is moveable between a closed position, wherein the valve closes the medicament delivery port, and an open position, wherein the medicament delivery port is open.

In another aspect, one embodiment of a ventilator circuit includes an oxygen supply communicating with the inlet port and an a user interface communicating with the outlet port. A medicament delivery device may be in communication with the medicament delivery port.

In another aspect, a method of delivering a medicament includes introducing a gas to an inlet port of an adapter along a flow path, circulating the gas around an exterior passageway defined by an exterior surface of an interior wall, wherein the interior wall is positioned transverse to the flow path of the inlet port, and passing the gas through a mouth of the interior wall into an interior passageway defined by an inner surface of the inner wall. The method further includes introducing a medicament through a medicament delivery port opening into the mouth and thereby entraining the medicament with the gas, and delivering the medicament to a user through an outlet port of the adapter communicating with the interior passageway.

The present embodiments of the invention, together with further objects and advantages, will be best understood by reference to the following detailed description taken in conjunction with the accompanying drawings.

BRIEF DESCRIPTION OF THE DRAWINGS

FIG. 6 is a cross-sectional view of one embodiment of an adapter with a valve in a closed position.

FIG. 7 is a cross-sectional view of one embodiment of an adapter with a valve in a open position.

FIG. 10 shows a perspective view of another embodiment of an adapter.

FIG. 11 shows the adapter of FIG. 10 in a ventilator circuit.

FIG. 16 shows a cross-sectional view of an adapter with a valve in a closed position.

FIG. 17 shows a cross-sectional view of an adapter with a valve in an open position.

FIGS. 19A-C show side and perspective views of the adapter shown in FIG. 18.

FIG. 20 shows an exploded perspective view of one embodiment of an adapter.

FIG. 21 shows a cross-sectional view of an adapter with a valve in a closed position.

FIG. 22 shows a cross-sectional view of an alternative embodiment of an adapter.

FIG. 25 shows a cross-sectional view of an alternative embodiment of an adapter.

FIG. 26 shows a cross-sectional view of an alternative embodiment of an adapter.

FIGS. 31A and B show cross-sectional and side views of an alternative embodiment of an adapter.

FIG. 34 shows a cross-sectional view of an alternative embodiment of an adapter.

FIG. 35 shows a cross-sectional view of an alternative embodiment of an adapter.

FIG. 36 shows a perspective view of one embodiment of an actuator.

FIGS. 37A and B show top and bottom perspective views of one embodiment of a port.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" ports may refer to any sequence of such members, and is not limited to the first and second ports of a particular configuration unless otherwise specified. It should be understood that the terms "input port" and "outlet port" refer to the function of the ports during an inhalation phase, and that the ports may serve the opposite function (removal or exit) during an exhalation phase. It should be understood that the term "communicates" refers to a fluid communication, and may be direct or indirect, for example through an intervening passageway.

Figure 5:
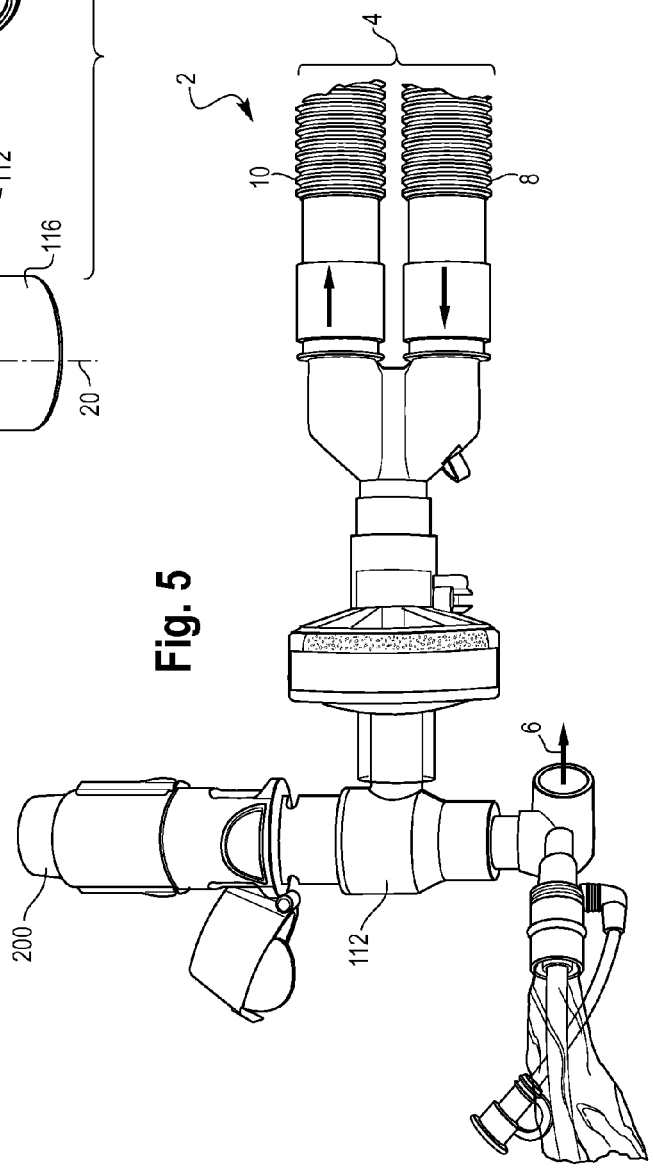
FIG. 5 is a view showing an adapter in a ventilator circuit.
Figure 9:
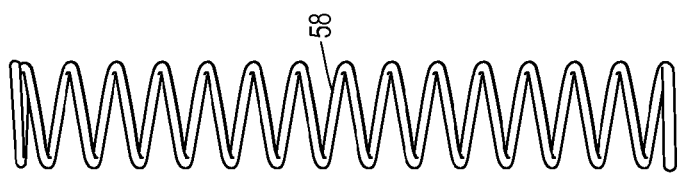
FIG. 9 shows a biasing spring for the valve.
Figure 8E:
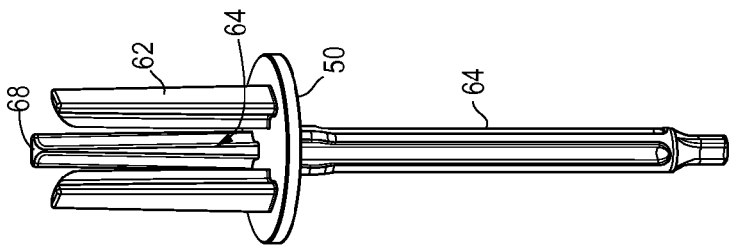
FIGS. 8A-E show different valve actuator embodiments.
Figure 8D:
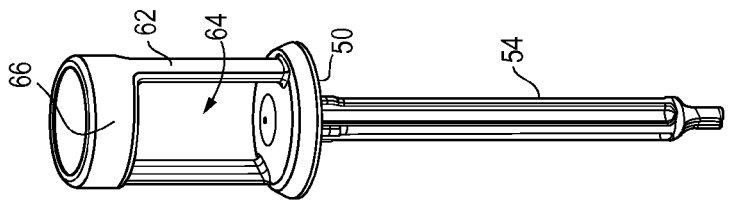
Figure 8C:
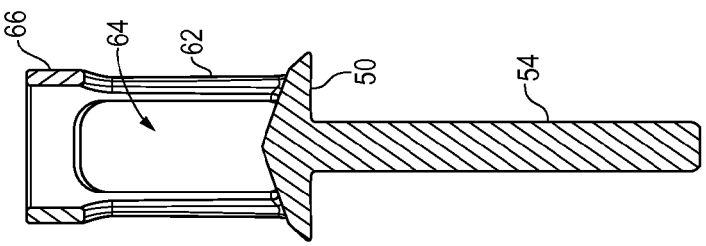
Figure 8B:
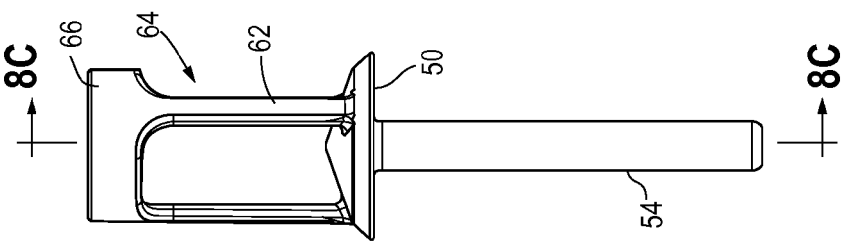
Figure 8A:
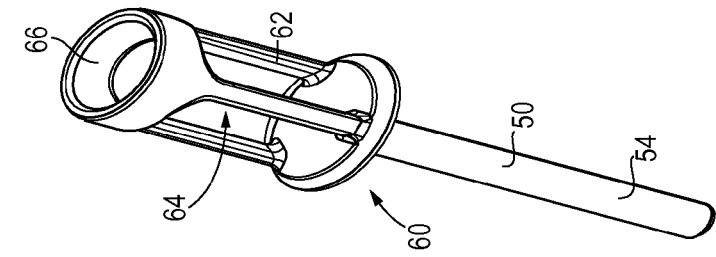
Figure 12B:
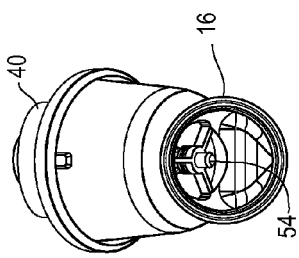
FIGS. 12A-E show cross-sectional, side, end and top views of the adapter shown in FIG. 10 with the valve in a closed position.
Figure 12D:
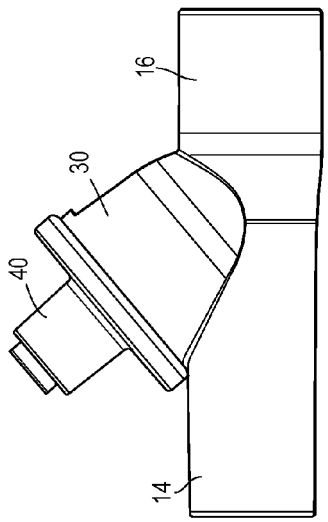
Figure 12A:
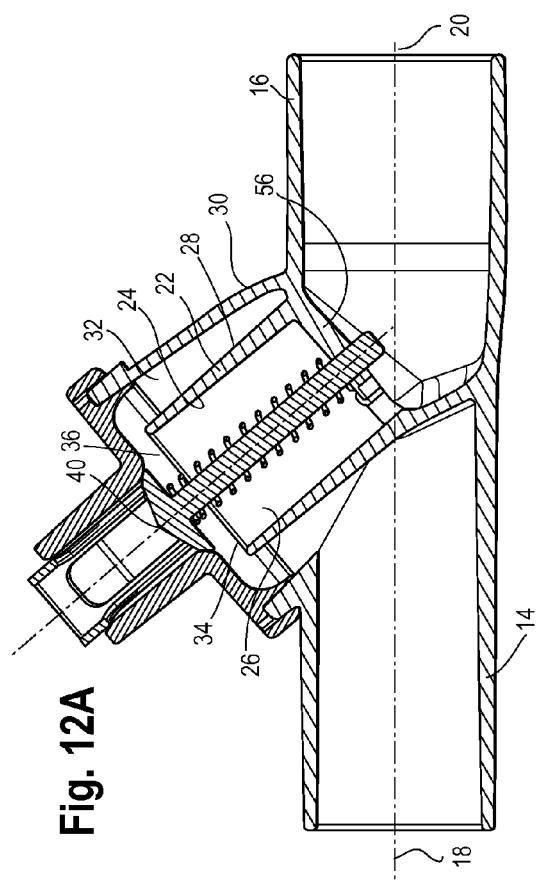
Figure 12C:
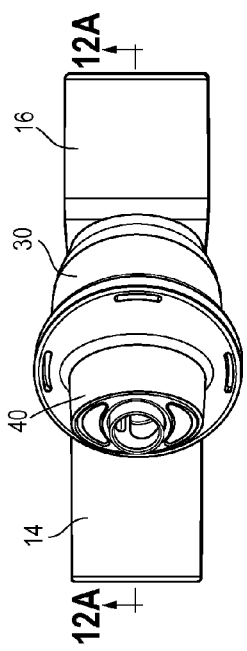
Figure 12E:
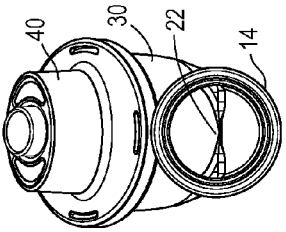
Figure 14:
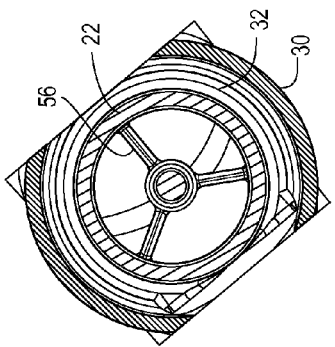
FIG. 14 shows a cross-sectional view taken along line 14-14 in FIG. 13.
Figure 13A:
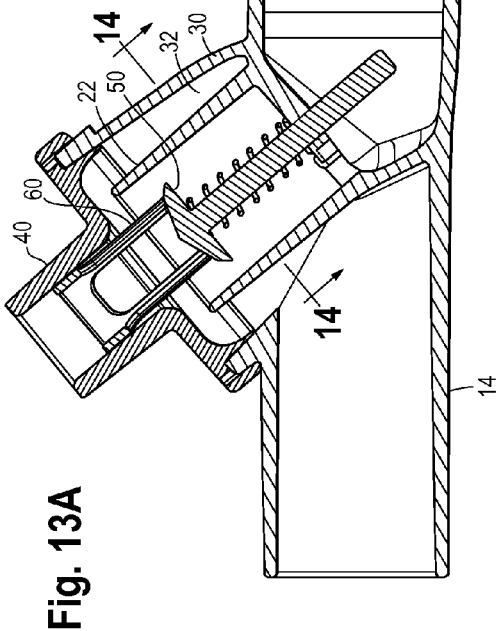
FIGS. 13A and B show cross-sectional views of the adapter shown in FIG. 10 with the valve in an open position and without the valve.
Figure 13B:
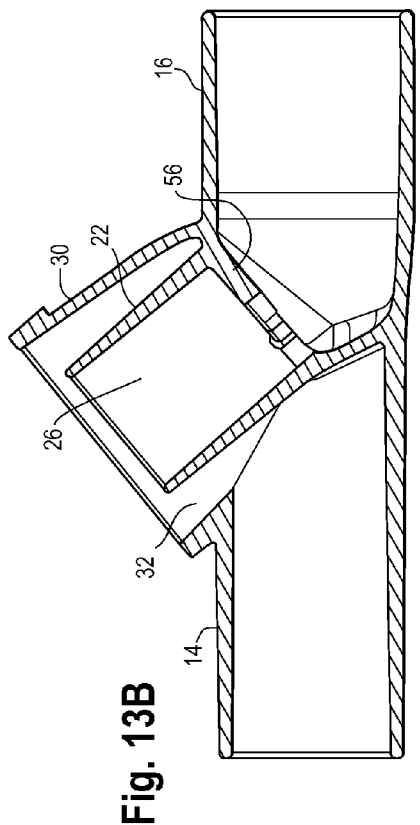
Figure 15:
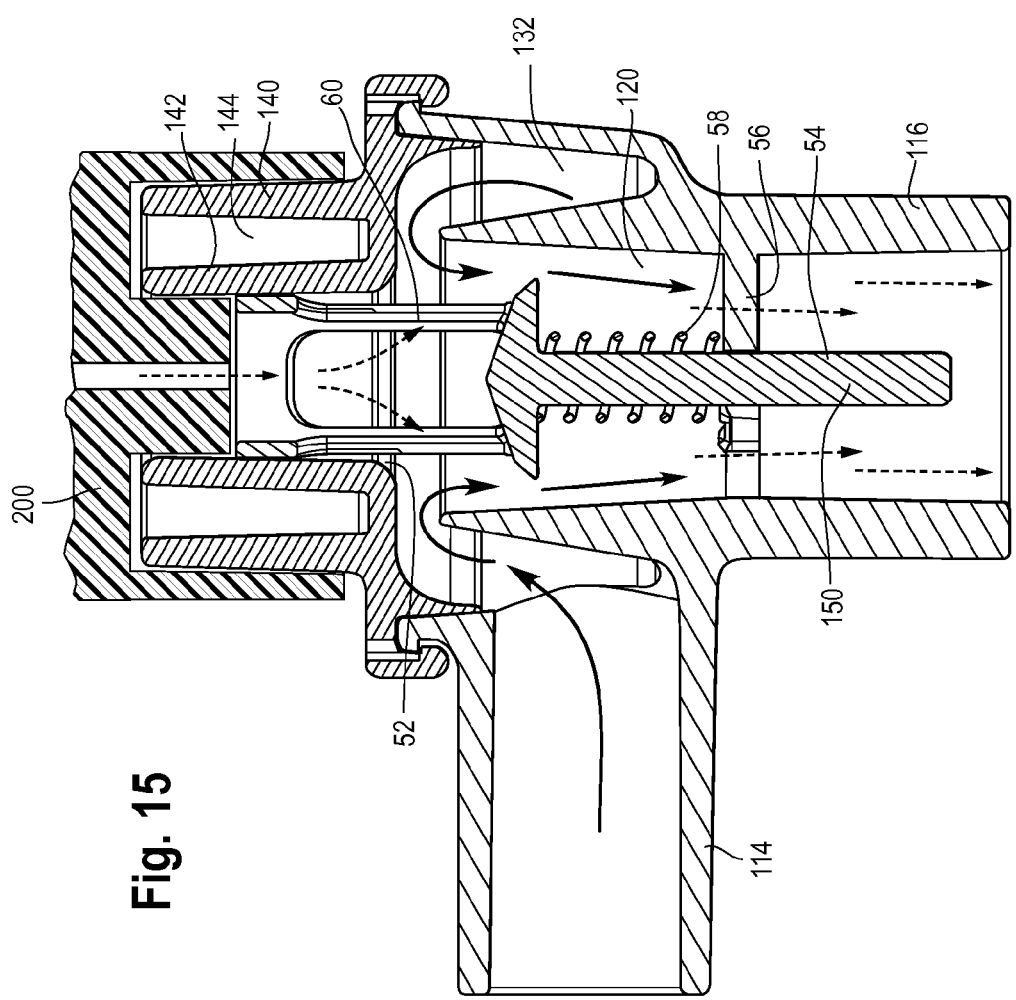
FIG. 15 shows a cross-sectional view of an adapter with a valve in an open position.

Referring to FIGS. 5 and 10, a ventilator circuit 2 is shown as including a ventilator 4 providing a gas supply, such as oxygen. Inlet and outlet lines 8, 10 may communicate with the ventilator 4. A user interface 6, such as a mask, tracheotomy tube, or mouthpiece is in communication with the gas supply.

Figure 1:
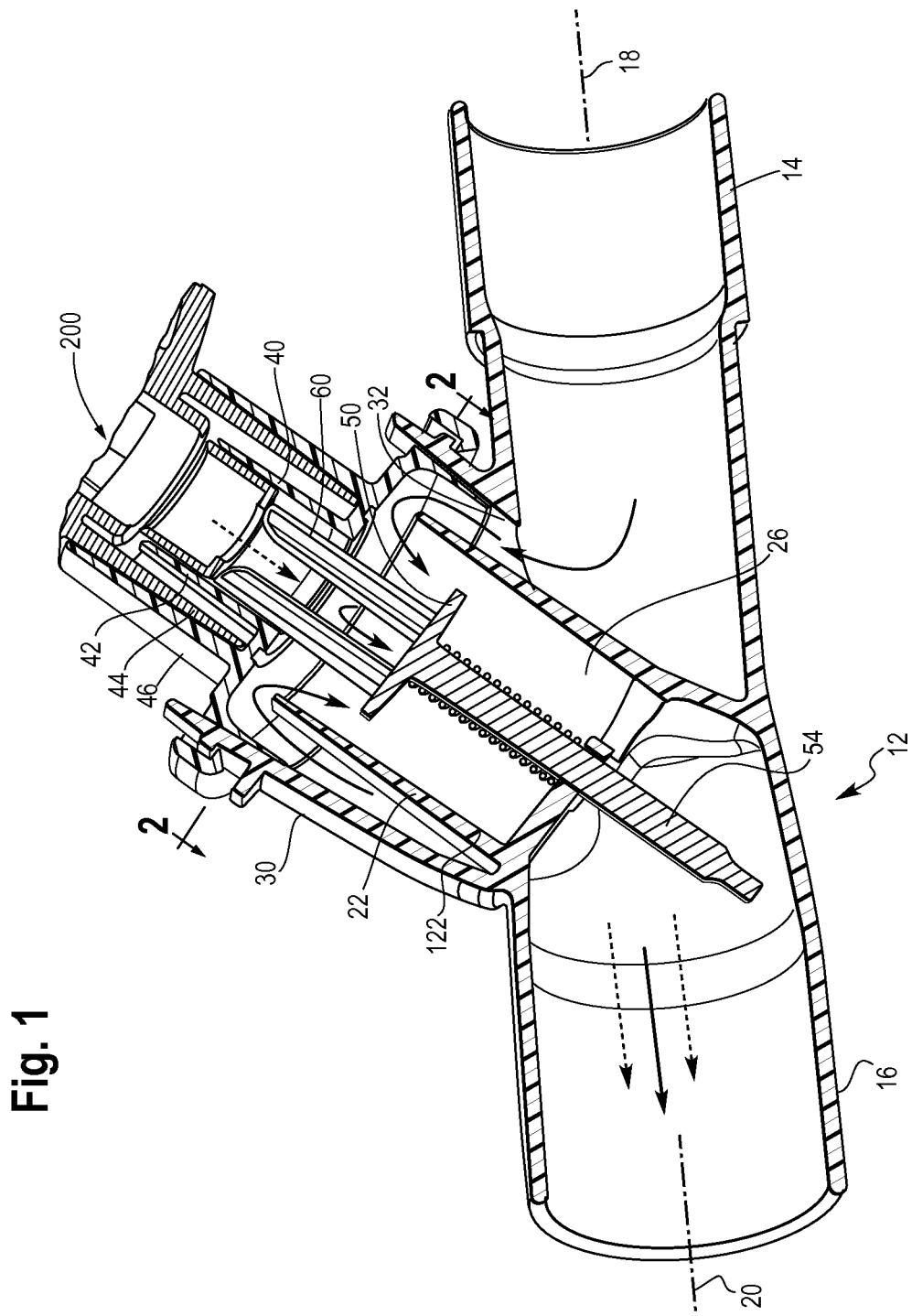
FIG. 1 is a cross-sectional view of an adapter with a medicament delivery device inserted therein.
Figure 2:
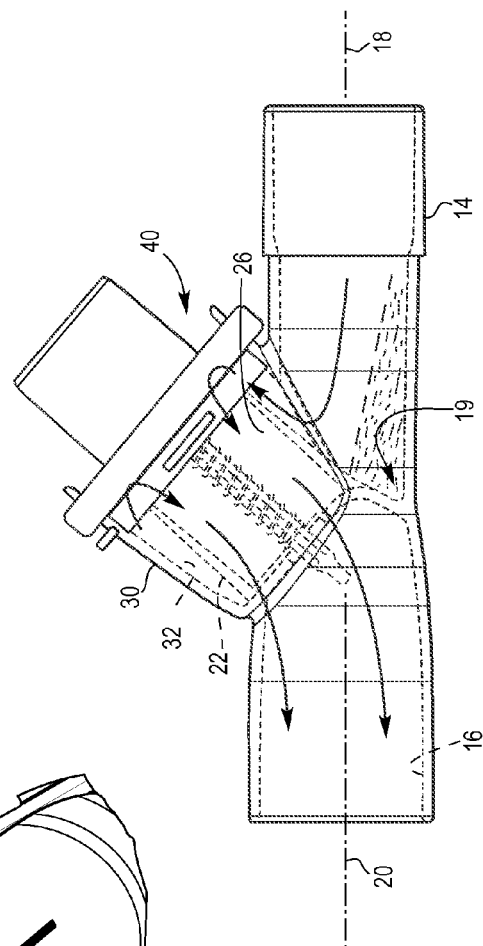
FIG. 2 is a top cross-sectional view taken along line 2-2 of FIG. 1.
Figure 3:
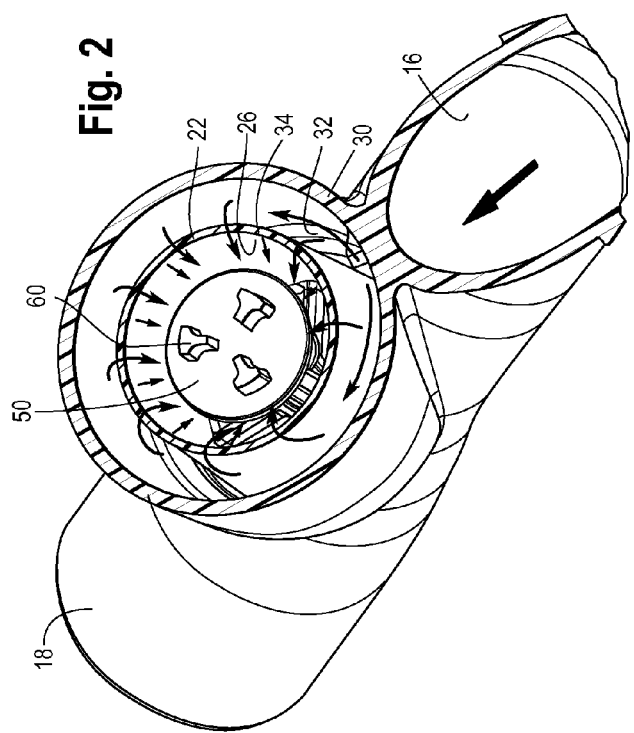
FIG. 3 is a cross-sectional view of the adapter shown in FIG. 1 with the valve closed.
Figure 4:
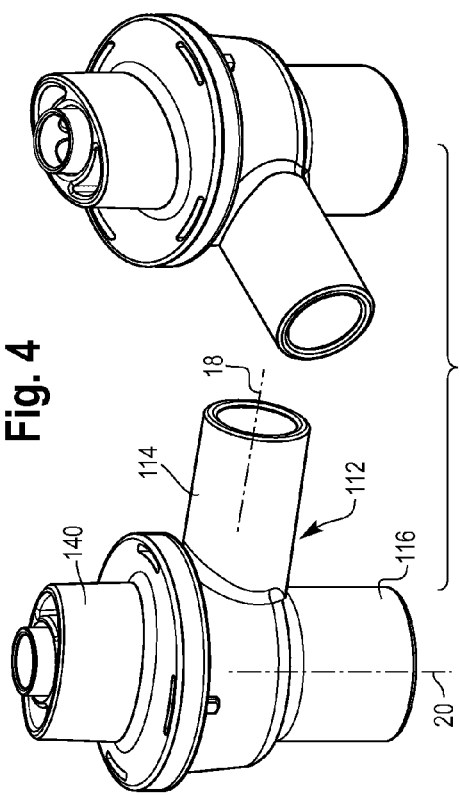
FIG. 4 is a perspective view of one embodiment of an adapter.

Referring to FIGS. 1-7, 10-26, and 33-35, the ventilator circuit also includes an adapter 12, 112 inserted in the flow path between the ventilator and the user interface. The adapter 12, 112 includes a housing having an inlet port 14, 114 defining a flow path and communicating with the ventilator 4, and an outlet port 16, 116 communicating with the user interface 6. The inlet port 14, 114 defines a flow path 18 that may be parallel to the flow path 20 of the outlet port as shown in FIG. 1, or extending transversely thereto, for example in an orthogonal relationship as shown in FIG. 4.

Referring to FIGS. 1-7, 10-26 and 33-35, the housing further includes an interior wall 22, 122 having an inner surface 24, 124 defining an interior passageway 26, 126 communicating with the outlet port and an exterior surface 28, 128 defining an exterior passageway 32, 132 communicating with the inlet port. An outer wall 30, 130 surrounds the inner wall and further defines the exterior passageway. The interior wall has a free end 34, 134 defining a mouth 36, 136 communicating between the interior and exterior passageways. The interior wall 22 is positioned transverse to at least a portion of the flow path 18 of the inlet port. The term "transverse" means lying or being across, for example the wall extends across the flow path of the inlet port, and is not limited to an orthogonal relationship. For example, the interior wall may extend orthogonal to the flow path as shown in FIG. 4, or may form an acute angle α (e.g. between about 40 and 60 degrees in various embodiments, and about 50 degrees in one embodiment) relative thereto as shown in FIG. 1. The wall may extend across the entirety of the cross-section of the flow path of the inlet port, as shown for example in FIGS. 4 and 12, or may extend across only a portion thereof.

Referring to FIGS. 1-7, 10-26 and 33-35, the adapter housing further includes a medicament delivery port 40 opening into at least one of the exterior and interior passageways 26, 32, for example at the mouth 36, above the mouth, or below the mouth. The port 40, 140 may include a central channel defining the delivery opening formed by an annular wall 42, 142, and a surrounding peripheral channel 44, 144 formed by another wall 46, 146. A valve 50 is moveable between a closed position, wherein the valve is seated on a valve seat 52 and closes the opening of the delivery port as shown in FIGS. 3, 6, 12A-E, 16, 21, 23, 28, and 33, and an open position wherein the medicament delivery port is open as shown in FIGS. 1, 2, 13, 15, 17, 24-26, 29, 30, 34 and 35. The valve includes a stem 54 that moves axially relative to a baffle or guide 56, 156 formed between the interior passageway 26, 126 and the outlet port 16, 116. A spring 58 is disposed around the valve stem 54 and biases the valve to a closed position against the seat 52 on the medicament delivery port. The port 40 may be configured as a cap member that closes the stop of the exterior passageway as shown in FIGS. 20 and 37A-38B.

Referring to FIGS. 1-7, 10-26 and 33-35, the exterior passageway 32, 132 extends around an entire periphery of the internal wall 22, 122, which means in one embodiment, the exterior passageway completely encircles the wall, formed as an annular wall, providing a 360 degree passageway around the wall.

An actuator 60 is attached to the end of the valve 50 as shown for example in FIGS. 8A-E and 36. In various embodiments, the actuator includes at least one side opening 64 formed therein. The actuator may be configured with a plurality of arms 62 (shown as two or three, although it could be more) defining a plurality of side openings 64 therebetween. A collar 66 may join the ends of the arms. The collar 66, or free ends 68, 69 of the arms, engage an end of the medicament delivery device 200.

Figure 18:
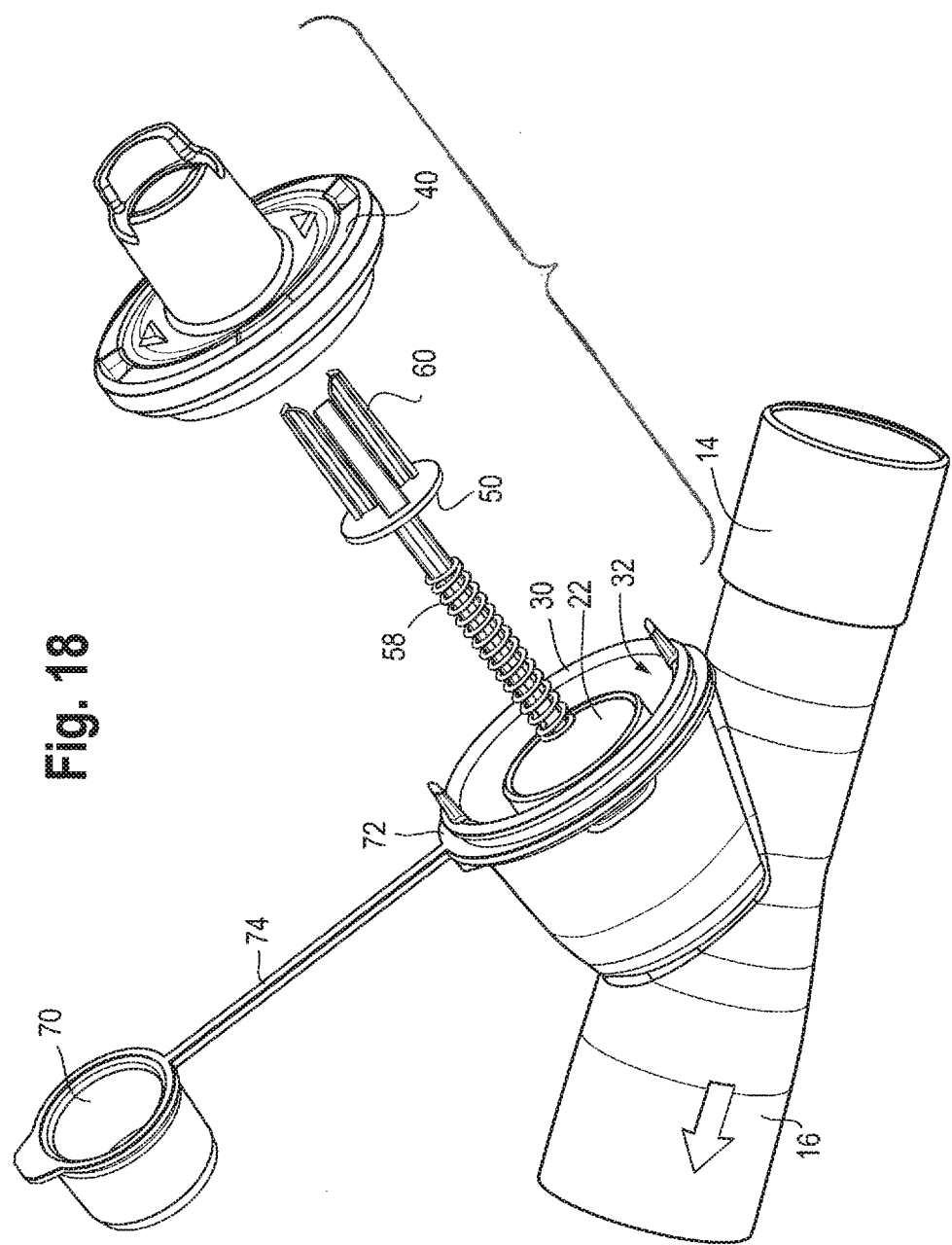
FIG. 18 shows an exploded view of one embodiment of an adapter.
Figure 24:
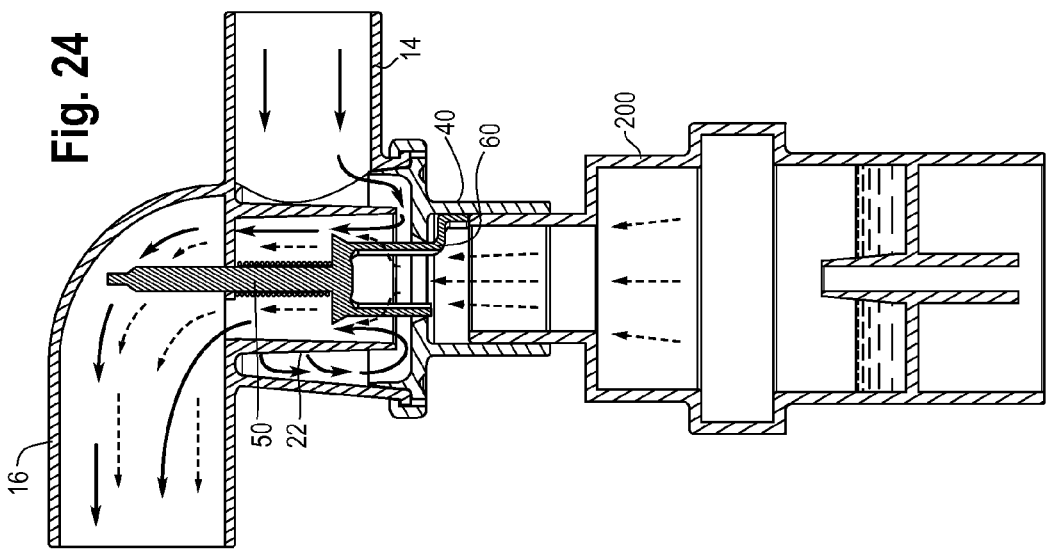
FIG. 24 shows a cross-sectional view of an alternative embodiment of an adapter.
Figure 23:
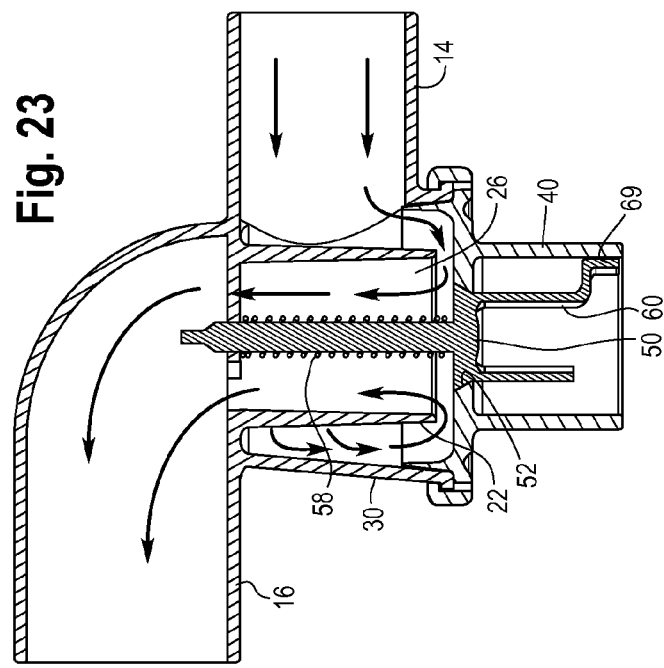
FIG. 23 shows a cross-sectional view of an alternative embodiment of an adapter.
Figure 38A:
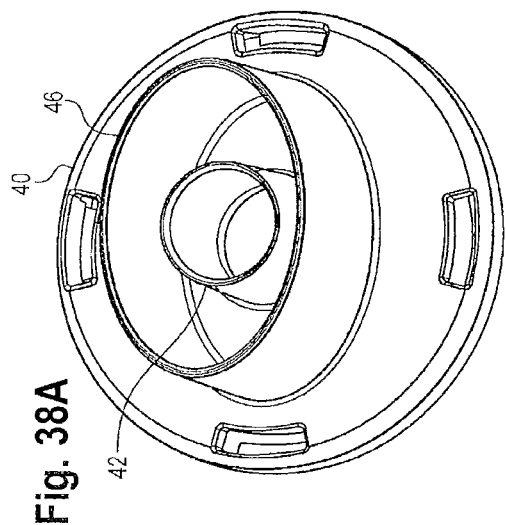
FIGS. 38A and B show top and bottom perspective views of one embodiment of a port.
Figure 38B:
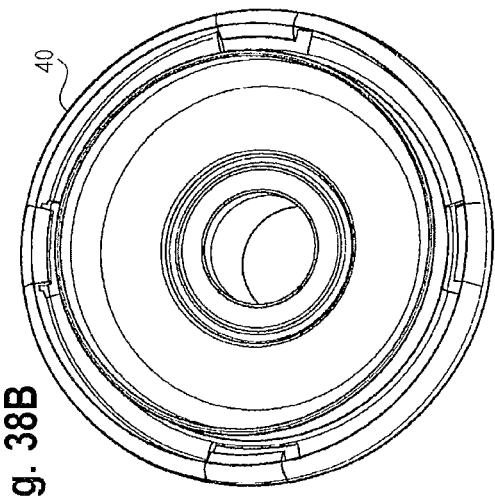
Figure 27:
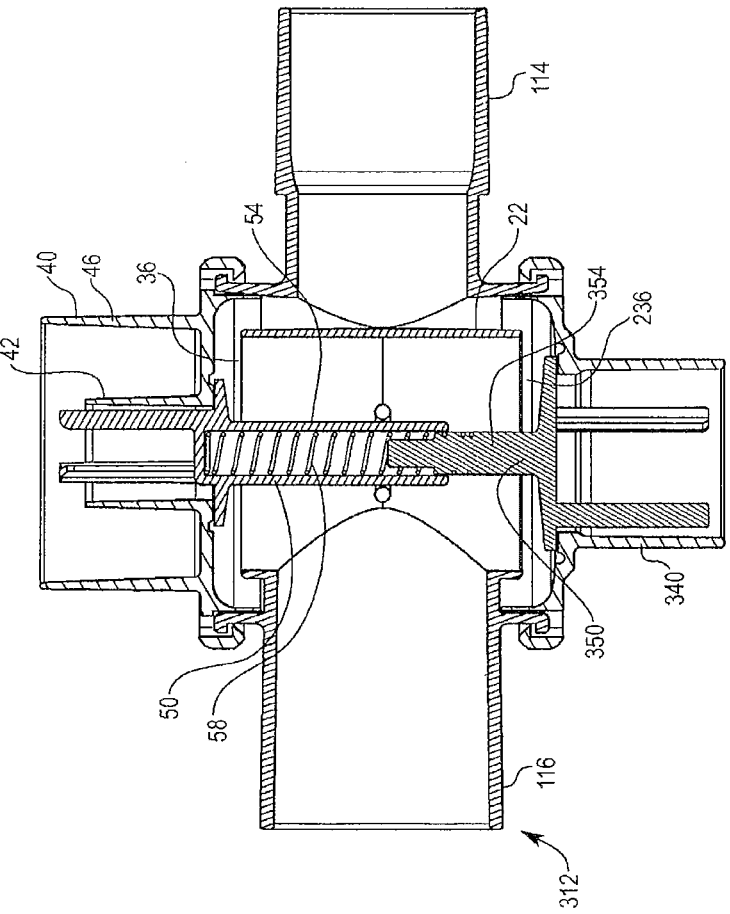
FIG. 27 shows a cross-sectional view of an alternative embodiment of an adapter.
Figure 28:
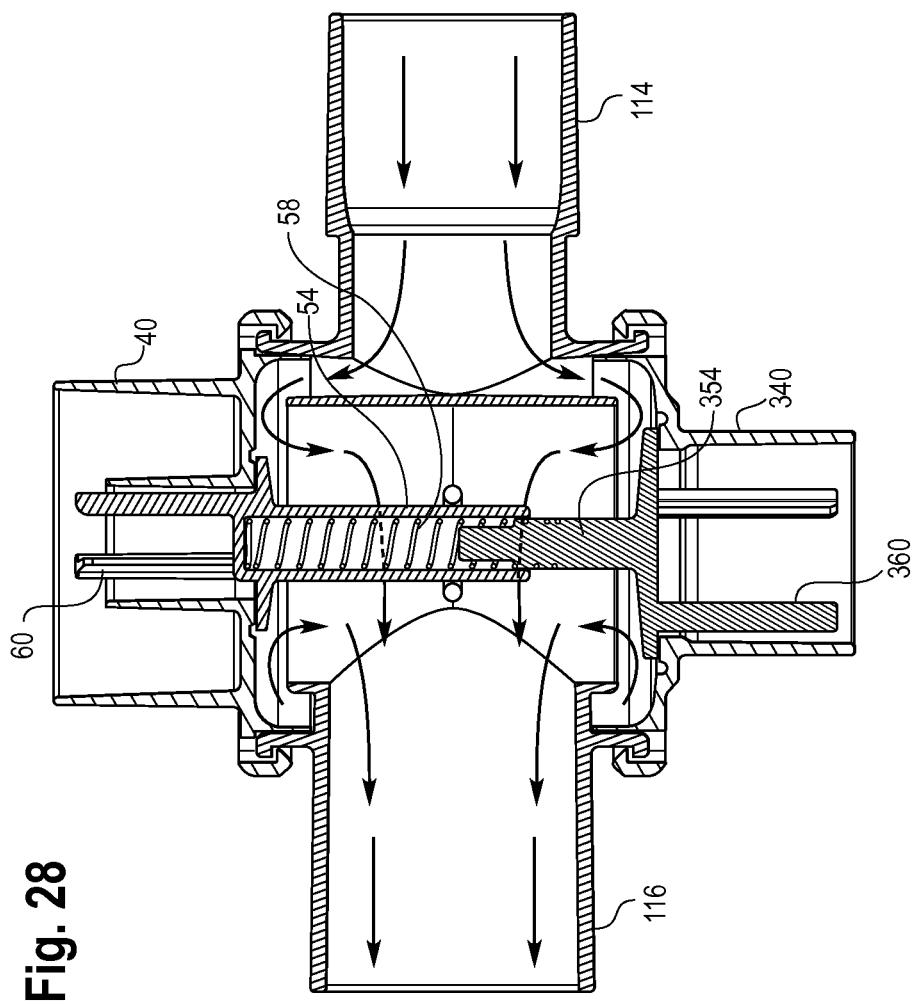
FIG. 28 shows a cross-sectional view of an alternative embodiment of an adapter.
Figure 30:
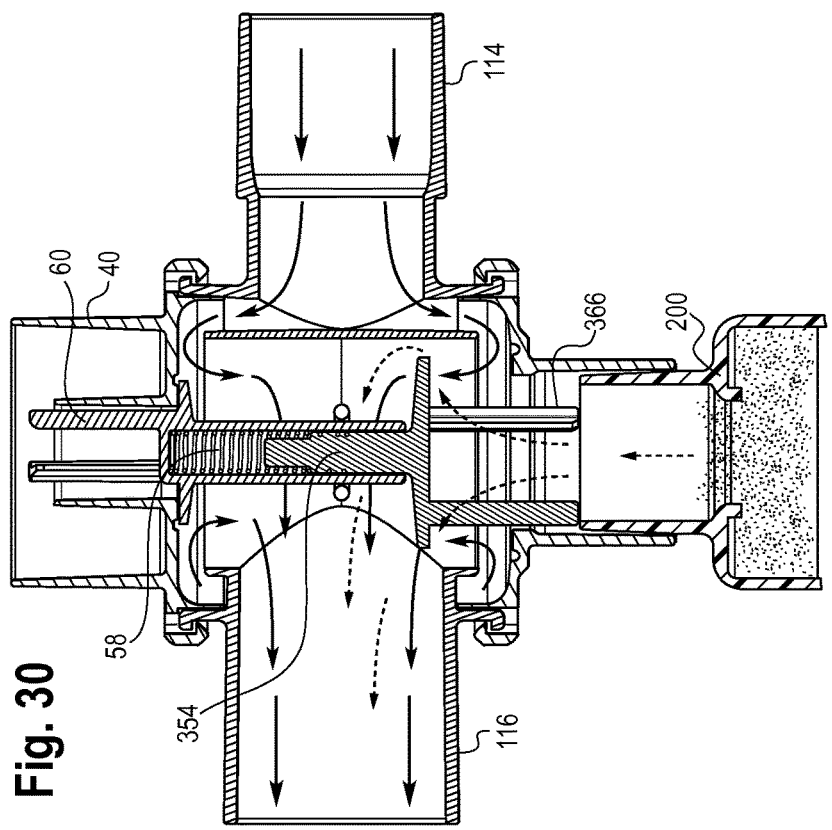
FIG. 30 shows a cross-sectional view of an alternative embodiment of an adapter.
Figure 29:
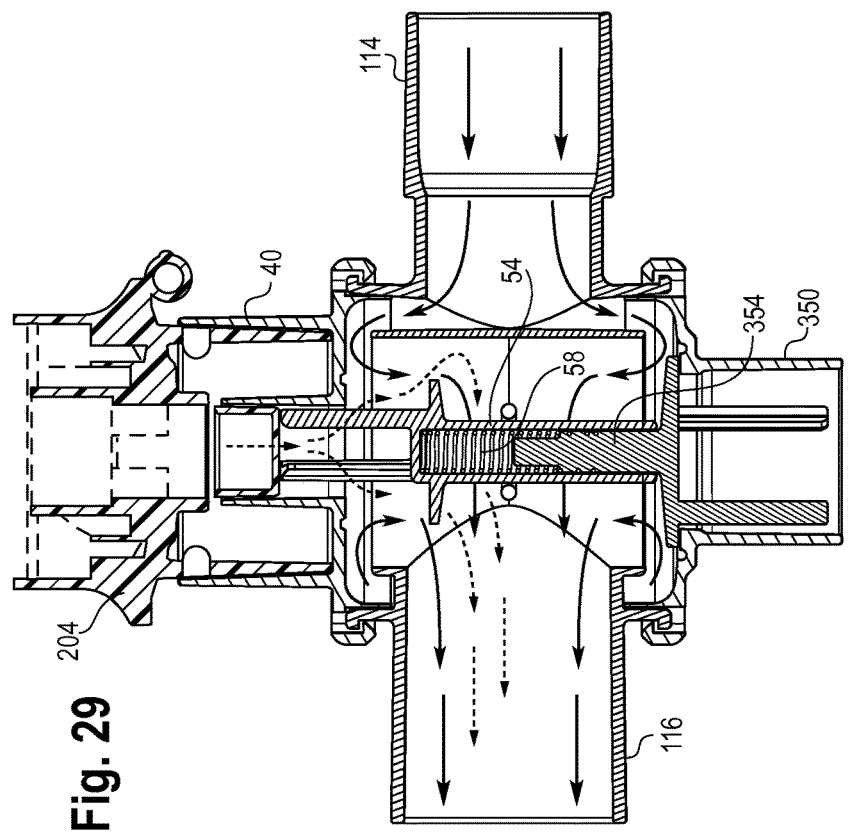
FIG. 29 shows a cross-sectional view of an alternative embodiment of an adapter.
Figure 33:
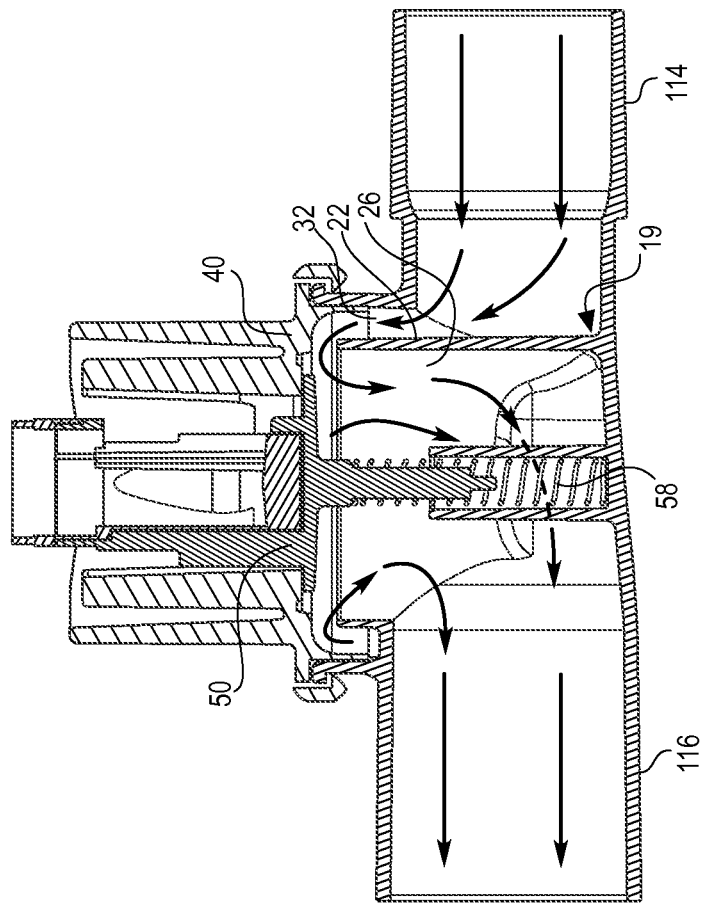
FIG. 33 shows a cross-sectional view of an alternative embodiment of an adapter.

Referring to FIGS. 18-20, a cap 70 may be tethered to the adapter with a retaining ring 72 and lanyard 74, and may be moved from an off position to an on position, wherein the cap covers the medicament delivery port 40 in the on position. The tethered cap 70 helps to maintain the ventilator circuit free from pressure leaks and dust particles.

Figure 32:
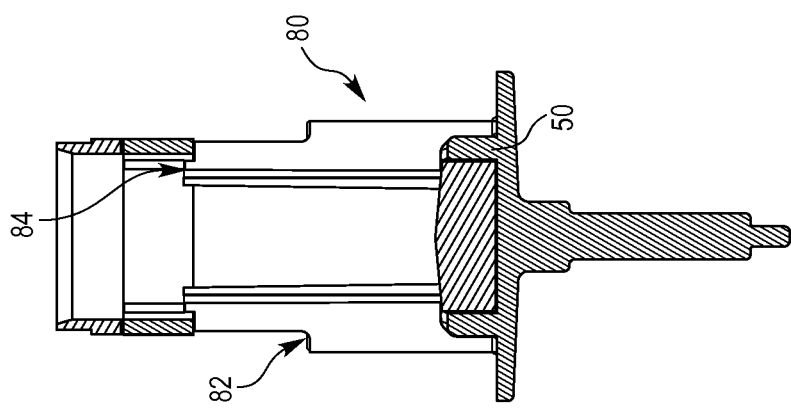
FIG. 32 shows a cross-sectional view of an alternative embodiment of an actuator.

The end 66, 68 of the actuator 60 and/or port 40 may be configured to engage different types and shapes of medicament delivery devices 200, including various nebulizers, a Hudson RCI Micro Neb nebulizer, an Aerogen AeroNeb Solo nebulizer, a Respimat inhaler, and/or other delivery devices. For example, as shown in FIG. 32, an actuator 80 is provided with two engagement members 82, 84, shown as an end portion and a shoulder, which are dimensioned to be engaged by different types of delivery devices. Various delivery device and adapters 90 may be configured with first ends 92 that fit into the port 40 and actuate the valve, and second ends 94 that are shaped to receive the particular delivery device. Other delivery devices interact directly with the port, for example with an annular flange that is inserted into a channel 144 formed around the port or inside the port as shown.

Referring to FIGS. 27A-30, an adapter housing 312 has first and second mouths 36, 236 communicating between the exterior passageway 32 and the interior passageway 26 on opposite ends of the interior wall 22. First and second medicament delivery ports 40, 340 are positioned adjacent the first and second mouths. The ports may have different dimensions and shapes to accommodate different types of medicament delivery devices, for example with the port 46 having a channel shaped to receive the end of one type of device and the port 346 configured to receive the device therein. A second valve 350 is configured to move between a closed position wherein second valve closes the second medicament delivery port and an open position wherein the second medicament delivery port is open. As shown, the second valve 350 is in a closed position when the first valve 50 is in an open position, and the first valve is in a closed position when the second valve is in an open position. It should be understood, however, that both valves may be moved to the open position simultaneously. The first and second valves may have interfacing valve stems 54, 354, with one stem moveable within the other, and with a spring 58 acting between the valve stems to bias the valves to the closed position.

In operation, and referring to FIGS. 1-7, 10-31B and 33-35, the adapter 12, 112, 312 is inserted into a ventilator circuit 2. A gas flows along the flow path 18 through the inlet port 14, 114, circulates around the internal wall 22, 122 in the exterior passageway 32, 132 and passes over the edge 34, 134 and through the mouth 36, 136 to the interior passageway 26, 126, and then to the outlet port 16, 116, whereinafter the gas may be communicated to the patient through the user interface 6.

When a caregiver desires to deliver a medicament to the patient, a medicament delivery device 200, whether a nebulizer 202, inhaler 204 or other device, is inserted into the medicament delivery port 40, 140. The insertion causes the medicament delivery device, or an adapter connected thereto, to engage the actuator 60 and press it inwardly against the biasing force of the spring 58, thereby opening the valve 50 as it is moved off of the seat 52. The medicament may thereafter be administered by actuating the medicament delivery device 200, or the insertion and actuation of the device against the valve may administer the medicament. The medicament is dispensed into the flow of gas. Because of the circumferential flow, e.g., 360 degree flow, around the wall and through the mouth, the medicament is thoroughly and uniformly mixed with the gas. The flow eliminates any unnecessary turbulence in the flow, thereby increasing the performance of the device. The configuration of the wall 22, and its interface with the inlet port 18, helps to collect water created by humidity in the circuit, in a pooling area 19 at the bottom of the wall such that the water does not adversely affect the drug performance. After the treatment, the medicament delivery device 200 may be removed from the medicament delivery port 40, with the valve 50 thereafter closing the medicament delivery port opening.

The adapter thereby provides a high efficiency drug delivery method in a closed ventilation circuit, and is robust and simple including only an adapter and medicament delivery device. The system can be installed, and thereafter used, in a quick and easy fashion. The valve ensures a low microbiological risk. The valve prevents contaminants from entering the system at an earlier point of the inhaler insert passage way. The ventilator circuit is kept sealed from outside contamination at all times with or without the medicament delivery device in place, and the adapter can be a permanent feature of the ventilator circuit, thereby eliminating the need to temporarily break the circuit and disconnect the patient from the ventilator. By having a permanent connection, any losses in pressure are minimized. Also hospital personnel cross contamination is minimized. The spring loaded valve when closed is fully seated and out of the way of the air stream, minimizing any resistance to the flow, and or any leaks to the outside of the ventilator circuit.

The adapter may be made of polypropylene and/or MABS/Terlux, and the valve spring may be made of stainless steel, or plastic.

When a medicament delivery device is not seated in the port, the inspiratory air stream produced by the ventilator flows around and over the 360 degree cylindrical chamber, defined by the wall, under the fully seated actuator valve around the spring, and through the three spoke actuator guide to the outlet port.

When a medicament delivery device 200 is inserted into the port 46, friction with the wall of the port holds the device in in place. The device pushes down the actuator and valve compressing the spring, and opening the passage where the drug flows out of the device. The inspiratory air stream produced by the ventilator flows around and over the 360 degree cylindrical chamber and carries the drug released by the inhaler. The air and drug mixture travel out of the cylindrical chamber through the three spoke actuator guide and to the outlet port of the adapter.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An adapter housing comprising:
an inlet port defining a flow path;
an outlet port;
an interior wall having an inner surface defining an interior passageway communicating with said outlet port and an exterior surface defining an exterior passageway communicating with said inlet port, and wherein said interior wall defines a mouth communicating between said interior and said exterior passageways, wherein said interior wall is positioned substantially transverse to at least a portion of said flow path of said inlet port, and wherein said exterior passageway is in fluid communication with said outlet port only through said interior passageway;
a medicament delivery port opening into at least one of said exterior passageway and said interior passageway; and
a valve moveable between a closed position wherein said valve closes said medicament delivery port and an open position wherein said medicament delivery port is open.

2. The adapter housing of claim 1 wherein said exterior passageway extends around an entire periphery of said internal wall.

3. The adapter housing of claim 2 wherein said exterior passageway extends 360 degrees around said internal wall.

4. The adapter housing of claim 1 wherein said valve comprises a spring biasing said valve to said closed position.

5. The adapter housing of claim 1 wherein said internal wall extends orthogonal to said flow path.

6. The adapter housing of claim 1 wherein said internal wall forms an acute angle relative to said flow path.

7. The adapter housing of claim 1 wherein said valve comprises an actuator having at least one side opening formed therein.

8. The adapter housing of claim 7 wherein said actuator comprises a plurality of arms defining a plurality of side openings therebetween.

9. An adapter housing comprising:
an inlet port defining a flow path;
an outlet port;
an interior wall having an inner surface defining an interior passageway communicating with said outlet port and an exterior surface defining an exterior passageway communicating with said inlet port, and wherein said interior wall defines a mouth communicating between said interior and said exterior passageways, wherein said interior wall is positioned substantially transverse to at least a portion of said flow path of said inlet port;
a medicament delivery port opening into at least one of said exterior passageway and said interior passageway; and
a valve moveable between a closed position wherein said valve closes said medicament delivery port and an open position wherein said medicament delivery port is open, wherein said valve comprises an actuator having at least one side opening formed therein, wherein said actuator comprises a first engagement surface adapted to engage a first medicament delivery device and a second engagement surface adapted to engage a second medicament delivery device.

10. An adapter housing comprising:
an inlet port defining a flow path;
an outlet port;
an interior wall having an inner surface defining an interior passageway communicating with said outlet port and an exterior surface defining an exterior passageway communicating with said inlet port, and wherein said interior wall defines a first mouth communicating between said interior and said exterior passageways, wherein said interior wall is positioned substantially transverse to at least a portion of said flow path of said inlet port, and wherein said interior wall further defines a second mouth communicating between said interior and said exterior passageway opposite said first mouth;
a first medicament delivery port opening into at least one of said exterior passageway and said interior passageway;
a second medicament delivery port opening into said second mouth;
a first valve moveable between a closed position wherein said first valve closes said first medicament delivery port and an open position wherein said first medicament delivery port is open; and
a second valve moveable between a closed position wherein said second valve closes said second medicament delivery port and an open position wherein said second medicament delivery port is open.

11. The adapter housing of claim 10 wherein said second valve is in a closed position when said first valve is in an open position, and wherein said first valve is in a closed position when said second valve is in an open position.

12. A ventilator circuit comprising:
an oxygen supply;
a user interface; and
an adapter comprising:
an inlet port defining a flow path and in flow communication with said oxygen supply;
an outlet port in flow communication with said user interface;
an interior wall having an inner surface defining an interior passageway communicating with said outlet port and an exterior surface defining an exterior passageway communicating with said inlet port, and wherein said interior wall defines a mouth communicating between said interior and said exterior passageways, wherein said interior wall is positioned substantially transverse to at least a portion of said flow path of said inlet port, and wherein said exterior passageway is in fluid communication with said outlet port only through said interior passageway;
a medicament delivery port opening into at least one of said exterior passageway and said interior passageway; and
a valve moveable between a closed position wherein said valve closes said medicament delivery port and an open position wherein said medicament delivery port is open.

13. The ventilator circuit of claim 12 wherein said exterior passageway extends around an entire periphery of said internal wall.

14. The ventilator circuit of claim 13 wherein said exterior passageway extends 360 degrees around said internal wall.

15. The ventilator circuit of claim 12 wherein said valve comprises a spring biasing said valve to said closed position.

16. The ventilator circuit of claim 12 wherein said internal wall extends orthogonal to said flow path.

17. The ventilator circuit of claim 12 wherein said internal wall forms an acute angle relative to said flow path.

18. The ventilator circuit of claim 12 wherein said valve comprises an actuator having at least one side opening formed therein.

19. The ventilator circuit of claim 18 wherein said actuator comprises a plurality of arms defining a plurality of side openings therebetween.

20. The ventilator circuit of claim 12 further comprising a medicament delivery device communicating with said medicament delivery port.

21. A ventilator circuit comprising:
an oxygen supply;
a user interface; and
an adapter comprising:
an inlet port defining a flow path and in flow communication with said oxygen supply;
an outlet port in flow communication with said user interface;
an interior wall having an inner surface defining an interior passageway communicating with said outlet port and an exterior surface defining an exterior passageway communicating with said inlet port, and wherein said interior wall defines a mouth communicating between said interior and said exterior passageways, wherein said interior wall is positioned substantially transverse to at least a portion of said flow path of said inlet port;

a medicament delivery port opening into at least one of said exterior passageway and said interior passageway; and a valve moveable between a closed position wherein said valve closes said medicament delivery port and an open position wherein said medicament delivery port is open, wherein said valve comprises an actuator having at least one side opening formed therein, wherein said actuator comprises a first engagement surface adapted to engage a first medicament delivery device and a second engagement surface adapted to engage a second medicament delivery device.

22. A ventilator circuit comprising:

an oxygen supply;

a user interface; and an adapter comprising:

an inlet port defining a flow path and in flow communication with said oxygen supply;

an outlet port in flow communication with said user interface;

an interior wall having an inner surface defining an interior passageway communicating with said outlet port and an exterior surface defining an exterior passageway communicating with said inlet port, and wherein said interior wall defines a first mouth communicating between said interior and said exterior passageways, wherein said interior wall is positioned substantially transverse to at least a portion of said flow path of said inlet port, and wherein said interior wall further defines a second mouth communicating between said interior and said exterior passageway opposite said first mouth;

a first medicament delivery port opening into at least one of said exterior passageway and said interior passageway;

a second medicament delivery port opening into said second mouth;

a first valve moveable between a closed position wherein said first valve closes said first medicament delivery port and an open position wherein said first medicament delivery port is open; and a second valve moveable between a closed position wherein said second valve closes said second medicament delivery port and an open position wherein said second medicament delivery port is open.

23. The ventilator circuit of claim 22 wherein said second valve is in a closed position when said first valve is in an open position, and wherein said first valve is in a closed position when said second valve is in an open position.

* * * * *